US010780149B2

(12) United States Patent
Marinelli et al.

(10) Patent No.: US 10,780,149 B2
(45) Date of Patent: Sep. 22, 2020

(54) THERAPEUTIC USE OF THE BOTULINUM NEUROTOXIN SEROTYPE A

(71) Applicant: Consiglio Nazionale Delle Ricerche, Rome (IT)

(72) Inventors: Sara Marinelli, Rome (IT); Flaminia Pavone, Rome (IT); Siro Luvisetto, Rome (IT); Valentina Vacca, Frosinone (IT)

(73) Assignee: CONSIGLIO NAZIONALE DELLE RICERCHE, Rome (IT)

( * ) Notice: Subject to any disclaimer, the term of this patent is extended or adjusted under 35 U.S.C. 154(b) by 0 days.

(21) Appl. No.: 16/252,972

(22) Filed: Jan. 21, 2019

(65) Prior Publication Data

US 2019/0224288 A1    Jul. 25, 2019

Related U.S. Application Data

(63) Continuation of application No. 15/568,668, filed as application No. PCT/IB2016/052280 on Apr. 21, 2016, now abandoned.

(30) Foreign Application Priority Data

Apr. 24, 2015    (IT) .................. 102015000013076

(51) Int. Cl.
| | | |
|---|---|---|
| *A61K 38/48* | (2006.01) | |
| *A61K 9/00* | (2006.01) | |
| *A61P 25/00* | (2006.01) | |

(52) U.S. Cl.
CPC ........ *A61K 38/4893* (2013.01); *A61K 9/0019* (2013.01); *A61K 9/0085* (2013.01); *A61P 25/00* (2018.01); *C12Y 304/24069* (2013.01)

(58) Field of Classification Search
None
See application file for complete search history.

(56) References Cited

U.S. PATENT DOCUMENTS

| | | | | | |
|---|---|---|---|---|---|
| 7,820,183 | B2 * | 10/2010 | Alvarez | ............. | A61K 38/4893 424/236.1 |
| 7,964,199 | B1 * | 6/2011 | Bigalke | ............... | A61K 38/4893 424/247.1 |
| 9,315,549 | B2 * | 4/2016 | Vazquez-Cintron | ........................ | C07K 14/001 |
| 10,016,491 | B2 * | 7/2018 | Bookbinder | ....... | A61K 39/3955 |
| 10,301,367 | B2 * | 5/2019 | Passananti | ............ | C07K 14/4705 |
| 2010/0124559 | A1 * | 5/2010 | Blumenfeld | ....... | A61K 38/4893 424/239.1 |
| 2012/0251574 | A1 * | 10/2012 | Blumenfeld | .......... | A61K 38/164 424/239.1 |
| 2014/0248237 | A1 * | 9/2014 | Bookbinder | ............ | A61K 38/47 424/85.5 |
| 2014/0349976 | A1 * | 11/2014 | Hacksell | ............ | A61K 31/4468 514/129 |
| 2015/0132282 | A1 * | 5/2015 | Finzi | ................... | A61K 38/4893 424/94.67 |
| 2016/0256531 | A1 * | 9/2016 | Finzi | ................... | A61K 38/4893 |
| 2017/0042834 | A1 * | 2/2017 | Westphal | ............. | A61K 31/165 |
| 2018/0043000 | A1 * | 2/2018 | Finzi | ................... | A61K 38/4893 |
| 2018/0140685 | A1 * | 5/2018 | Marinelli | ............. | A61K 9/0019 |
| 2019/0136216 | A1 * | 5/2019 | Dong | ..................... | C07K 14/33 |
| 2019/0224288 | A1 * | 7/2019 | Marinelli | ............. | A61K 9/0085 |
| 2019/0365873 | A1 * | 12/2019 | Finzi | ................... | A61K 31/5513 |

FOREIGN PATENT DOCUMENTS

| | | | | | |
|---|---|---|---|---|---|
| CA | | 2521177 | A1 * | 11/2004 | ......... A61K 38/4893 |
| EP | | 3285800 | A1 * | 2/2018 | ......... A61K 9/0019 |
| WO | WO-2008000490 | A1 * | 1/2008 | ......... A61K 38/4893 |
| WO | WO-2008133884 | A2 * | 11/2008 | ......... A61K 31/4439 |
| WO | WO-2009018643 | A2 * | 2/2009 | ......... A61K 38/1703 |
| WO | WO-2009039461 | A2 * | 3/2009 | ........... C07D 211/58 |
| WO | WO-2014078724 | A1 * | 5/2014 | ............. A61K 45/06 |
| WO | WO-2016170501 | A1 * | 10/2016 | .............. A61P 25/00 |
| WO | WO-2017066705 | A1 * | 4/2017 | ........... C07D 405/14 |

OTHER PUBLICATIONS

Bentivoglio et al, Toxicon, 2015, 107:77-84. available online: Aug. 7, 2015 (Year: 2015).*
Chen et al, Toxins, 2012, 4:913-939. published: Oct. 19, 2012. (Year: 2012).*
Naicker et al, Journal of Orthopaedic Surgery, Apr. 2009, 17/1:96-99. (Year: 2009).*
Krishnan, Journal of Neurological Disorders, 2013, vol. 134, Issue 4, 6 pages: (Year: 2013).*
Richardson et al, Clinical Rehabilitation, 1997, 11:288-291 (Year: 1997).*
Catz et al, Eura Medicophys., 2007. 43:319-325. E-pub ahead of print on May 28, 2007 (Year: 2007).*
Marinelli et al, Neuroscience, 2010, 171:316-328 (Year: 2010).*
Santamato et al, J. Rehabil Med., 2010. 42:891-894 (Year: 2010).*
Finocchiaro et al, Toxins, 2018, 10, 128, doi:10.3390/toxins10030128. 17 pages. Published:Mar. 18, 2018 (Year: 2018).*
Marinelli et al, PloS One 7(10): e47977. doi:10.1371/journal.pone.0047977. 12 pages. Published: Oct. 24, 2012 (Year: 2012).*
Marinelli et al, Scientific Reports. 9:8883|https://doi.org/10.1038/s41598-019-45037-x. 17 pages. Published online: Jun. 20, 2019 (Year: 2019).*
Pavone et al, Toxins, 2010, 2:2890-2913, 25 pages. Published: Dec. 21, 2010 (Year: 2010).*

(Continued)

*Primary Examiner* — Nita M. Minnifield

(74) *Attorney, Agent, or Firm* — MacMillan, Sobanski & Todd, LLC

(57) ABSTRACT

A new therapeutic use of botulinum neurotoxin serotype A (Bont/A) is described, in the therapeutic treatment of paralysis caused by spinal cord injury.

6 Claims, 6 Drawing Sheets

(56) References Cited

OTHER PUBLICATIONS

Figure 1:
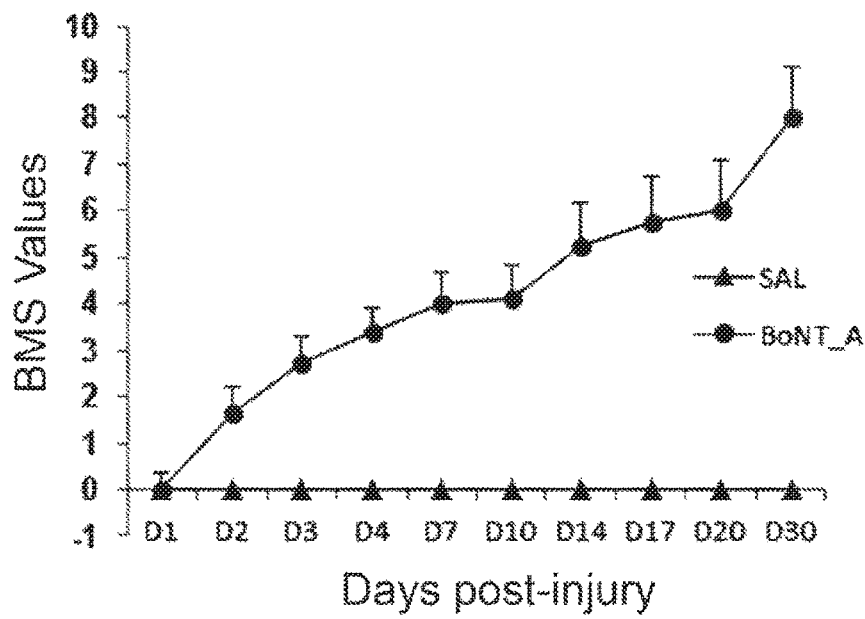
Figure 1:
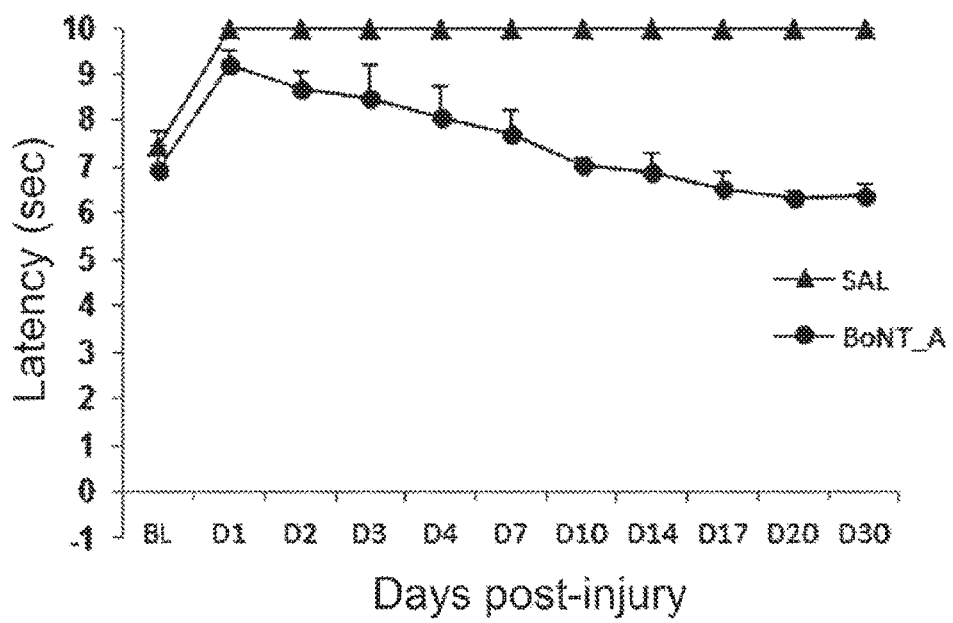

Krishnan, Current Drug Therapy, 2009, 4/2:101-105 (Year: 2009).*
Al-Khodairy et al, Spinal Cord. 1998, 36:854-858 (Year: 1998).*
Han et al, Spinal Cord. 2014. 52:S5-S6. (Year: 2014).*
Intiso et al, J. Rehabil. Med., 2009, 41:1100-1102 (Year: 2009).*
Spiegl et al, GMS Interdisciplinary Plastic and Reconstructive Surgery DGPW, 2014, vol. 3, 5 pages. Published: Dec. 10, 2014 (Year: 2014).*

* cited by examiner

A

B

FIG. 4

THERAPEUTIC USE OF THE BOTULINUM NEUROTOXIN SEROTYPE A

CROSS-REFERENCE TO RELATED APPLICATIONS

This is a continuation of U.S. Ser. No. 15/568,668 filed Oct. 23, 2017, still pending, national stage application filed under 35 U.S.C. § 371 of international application PCT/IB2016/052280, filed under the authority of the Patent Cooperation Treaty on Apr. 21, 2016, published; which claims the benefit of Italy Patent Application No. 102015000013076, filed on Apr. 24, 2015. The entire disclosures of all the aforementioned applications are expressly incorporated herein by reference for all purposes.

The present invention relates to a new therapeutic use of the botulinum neurotoxin serotype A.

The botulinum neurotoxin (BoNT), produced by the anaerobic bacterium *Clostridium botulinum*, consists of an amino acid heavy chain (HC=heavy chain) of 100 kDa and a light chain (LC=light chain) of 50 kDa linked one another by a disulfide bridge. The integrity of this bond is essential for the activity of the complex, making it extremely sensitive to environmental factors.

The botulinum neurotoxin, in its different serotypes (A-G), has been used in the clinical practice for several years for the most varied syndromes and pathologies: in the treatment of muscular pathologies, pain syndromes and for the treatment of symptoms of neurodegenerative diseases. Moreover, its use in cosmetics is already widespread.

The general mechanism by which BoNT is able to act on such a wide range of diseases is currently not fully understood, but it is known that this neurotoxin is able to reversibly block the release of many neurotransmitters/neuromodulators from nerve endings. In fact, it acts by cutting various components of the protein complex designated as SNARE. The latter, present in all cells, is essential in the exocytosis process when the synaptic vesicles must be anchored to the synaptic membrane from which the neurotransmitters will be released. The block of the formation of the SNARE complex prevents exocytosis and thereby transmission is inhibited.

Recently, attention has been focused on the ability of the botulinum neurotoxins not only to block acetylcholine but also various other neurotransmitters, such as glutamate, GABA and neuropeptides, such as SP and CGRP.

The heavy chain of the botulinum neurotoxin is particularly important for the penetration of the same inside the axonal ends. After the binding of the heavy chain with the terminal axon proteins, the neurotoxin can enter the neurons by endocytosis. The binding of the heavy chain occurs with the SV2 protein receptor, whose expression is increased when the synapse is more active. The light chain is able to leave the endocytic vesicles and reach the cytoplasm. The neurotoxin light chain has protease activity.

The botulinum neurotoxin serotype A (BoNT/A) proteolytically degrades the SNAP-25 protein, a type of SNARE protein. The protein SNAP-25 is required for the release of the neurotransmitters from the axon terminals. In particular, the botulinum neurotoxin degrades the SNAREs by preventing the release of the neurotransmitters at the synapses.

The botulinum neurotoxin (BoNT) is a powerful biological toxin which is widely used in the clinical practice for the treatment of the most varied diseases, including dystonias, such as spasticity due to spinal cord injury, headaches and bladder hyperactivity disorders.

More recently, BoNT has raised interest in the treatment of pain syndromes.

The present inventors had previously shown that the botulinum neurotoxin serotype A (BoNT/A) contrasts effectively neuropathic pain caused by nerve injury. In fact, BoNT/A has analgesic and anti-inflammatory properties due to its ability to block the release of pro-inflammatory factors, such as substance P and glutamate. It can also be retrogradely transported and act on glial cells (Schwann cells, astrocytes and microglia), as well as on neurons (Marinelli S, Vacca V, Ricordy R, Uggenti C, Tata A M, et al. (2012) The Analgesic Effect on Neuropathic Pain of Retrogradely Transported botulinum Neurotoxin A Involves Schwann Cells and Astrocytes. PLoS ONE 7(10): e47977).

A review of the clinical uses of botulinum neurotoxins and their mechanisms of action is found in Sheng Chen, Toxins 2012, 4, 913-939.

As for the patent literature related to botulinum neurotoxins and their therapeutic uses, we highlight the following prior art.

The U.S. Pat. No. 7,964,199 describes a pharmaceutical composition comprising a botulinum neurotoxin selected from serotypes A, B, C, D, E, F or G or a mixture of two of the above botulinum neurotoxins, for use in the therapeutic treatment of a neurological disorder selected from dystonia, spasmodic torticollis, blepharospasm, spasticity, migraine, lumbosciatica, spine disorders, and hypersalivation.

The International patent application WO 2006/013357 describes a composition or medicament comprising the botulinum neurotoxin serotype A2 and a surfactant, for use in the treatment of ophthalmological disorders, movement disorders, ENT disorders, gastrointestinal disorders, urogenital disorders, dermatological disorders, pain, inflammatory disorders, secretory disorders, respiratory disorders, hypertrophic disorders, articular disorders, endocrine disorders, autoimmune diseases, proliferative diseases, traumatic injuries, and veterinary disorders.

The International patent application WO 2009/80313 describes the use of BoNT/A in the therapy for spasticity due to spinal and cerebrovascular trauma. The use of the botulinum neurotoxin serotype A for the treatment of spasticity is also described in US patent application US 2010/0124559.

One of the salient features of botulinum neurotoxins, in particular of the botulinum neurotoxin serotype A, is the duration of action in patients (from 2 to 6 months) at very low concentrations, in the fM or pM range. Although the mechanisms of the persistence of the effect are not clear, however, the duration of the intracellular enzymatic activity of the botulinum neurotoxin serotype A in rat spinal cord neurons was shown to be at least 10 months. This feature gives the botulinum neurotoxin serotype A a considerable advantage compared to common drugs, which need to be administered continuously so that the therapeutic effect is maintained.

Only five pharmaceutical preparations containing the botulinum neurotoxin are currently available on the market, four of which containing BoNT serotype A (Botox®, Dysport®, Xeomin® and CBTXA), and one containing BoNT serotype B (Myobloc®/NeuroBloc®). The approval process is extremely complex and varies from one preparation to another and from one country to another. Currently, CBTXA is marketed only in China and little information is available on this product. Xeomin® was approved recently in Germany. The only BoNT/B marketed preparation (Myobloc®/NeuroBloc®) has just been approved for cervical dystonia (CD) and only in a few countries. Its use is limited to patients who have developed neutralising antibodies against BoNT/A preparations.

Botox® is the most widely accepted and widespread preparation in the world, followed by Dysport® which, however, has not yet been approved in the United States of America.

As described in greater detail below, the present inventors have now surprisingly found that the botulinum neurotoxin serotype A is effective in the therapeutic treatment of paralysis caused by spinal cord injury.

This observation is quite surprising in the light of the hitherto known therapeutic activities of the botulinum neurotoxin, such as in particular the treatment of spasticity.

Therefore, an object of the present invention is the botulinum neurotoxin serotype A for use as defined in appended claim 1, i.e. the therapeutic treatment of paralysis caused by spinal cord injury. In a preferred embodiment, the paralysis caused by spinal cord injury is paraplegia or tetraplegia.

Within the scope of the present invention is also a pharmaceutical composition comprising a pharmaceutically effective amount of the botulinum neurotoxin serotype A and at least one pharmaceutically acceptable carrier, excipient or diluent, for use in the therapeutic treatment of paralysis caused by spinal cord injury, particularly paraplegia or tetraplegia.

Additional features of the invention are identified in the appended dependent claims, which form an integral part of the present description.

In a preferred embodiment of the present invention, the botulinum neurotoxin serotype A is selected from the group consisting of botulinum neurotoxin serotype A1 and botulinum neurotoxin serotype A2.

In another preferred embodiment, the therapeutic treatment comprises administering to a human patient a pharmaceutically effective amount of the botulinum neurotoxin serotype A. According to this embodiment, a pharmaceutically effective amount of botulinum neurotoxin serotype A is in the range of 75 U-360 U.

It is to be understood that the therapeutically effective doses of botulinum neurotoxin vary depending on the particular preparation of the neurotoxin used. Although the two most widespread commercial products both contain serotype A (Botox® and Dysport®), one unit of Botox® is not equivalent to one unit of Dysport®. On the basis of available studies, it was established that the dose ratio of Botox®: Dysport® is in the range of 1:3 to 1:5. The dose ratio for Botox®:Xeomin® is estimated at 1:1.

It is therefore useful to recall that the neurotoxin dose indicated for each preparation refers exclusively to that specific preparation.

The dose of neurotoxin related to Botox® is often used as a reference value.

In the present specification, the pharmaceutically effective dose of BoNT/A is thus expressed as units (U) related to Botox®.

The botulinum neurotoxin serotype A may be administered as a single dose or as a cumulative dose, divided over a predetermined period of time so as to optimize the therapeutic effect. The determination of the administration regime falls within the skills of a person of average skill in the art.

The botulinum neurotoxin serotype A may be administered in any suitable manner, but the preferred administration mode is by injection. In a particularly preferred embodiment, the botulinum neurotoxin serotype A is administered intrathecally, more preferably by injection into the vertebral area immediately caudal to the area affected by the spinal cord injury.

The experimental section that follows is provided for illustration purposes only and does not limit the scope of the claims as defined in the appended claims.

EXPERIMENTAL SECTION

In the present invention a murine model of spinal cord injury was used, which accurately mimics the tissue damage resulting from a direct mechanical trauma and allows for reproducing the features of various human diseases caused by spinal cord injury ("Spinal Cord Injury", SCI), including the total absence of motor recovery.

First of all, preliminary experiments were carried out on male and female CD1 mice, in order to identify the correct parameters capable of inducing a severe SCI, as graded on the BMS scale ("Basso Mouse Scale", described in detail below) and to identify the most suitable subjects. The results of these experiments are reported in Table 1.

TABLE 1

| | TIPS | RESIDENCE TIME | SPEED | DEPTH |
|---|---|---|---|---|
| MILD | Rounded 1-2 | 300/500 ms | 3 m/sec | 2.5-3 mm |
| MODERATE | Rounded 3 | 500/600 ms | 3 m/sec | 3.5-5 mm |
| SEVERE | Rounded 4 | 600/1000 ms | 3 m/sec | 5 mm |

The present inventors demonstrated that the botulinum neurotoxin serotype A represents an effective treatment for paralysis caused by spinal cord injury (SCI).

Although the initial damage induced by SCI is attributable directly to trauma (haemorrhage, membrane disruption, vascular damage), the final pathohistological injury is much greater than that detectable in the first hours after the trauma. The spread of the damage is believed to be due to activation of a series of adverse events that lead to dysfunction and cell death. This cascade of injury-induced destructive events is defined as secondary injury. These events implicated astrocytes, which play a role in all the afflictions of the central nervous system and are involved in neuroinflammation.

After the SCI, the astrocytes contribute to the inhibitory environment inside the injured spinal cord: subsequent proliferation and hypertrophy thereof occur around the injury site. The reactive astrocytes form astroglial scarring that acts as a barrier to axon regeneration. According to opposed observations, scar formation by astrocytes is essential to provide protection to the neurons after a lesion of the central nervous system, so there must be a balanced reaction, possibly modulated pharmacologically, to promote axon regeneration.

Moreover, SCI initiates biochemical cascades that lead to an increase in the extracellular concentration of glutamate, resulting in excitotoxic events mediated by the glutamate receptor. After its release, specific transport proteins rapidly remove the extracellular glutamate from the synaptic cleft. The removal of excess glutamate prevents accumulation under normal conditions. However, with SCI, the concentration of extracellular glutamate increases up to neurotoxic levels. Excitotoxicity refers to the ability of glutamate to destroy neurons due to a prolonged excitatory synaptic transmission.

In the central nervous system, apoptosis mainly involves non-neuronal cells such as oligodendrocytes (ODs). Apoptotic cells are greater in number and closer to the epicentre of the lesion. Apoptosis of ODs leads to chronic demyelination, thus causing anterograde neurodegeneration. Moreover, SCI induces decreased expression of several myelin proteins. Recovery of ODs and preservation of myelin are expected to have a big effect on the functional outcome after SCI.

The evidence obtained by the present inventors, described in detail below, indicates that BoNT/A can be an effective treatment of SCI-caused paralysis as: (i) it is able to protect neuronal cells from excitotoxicity after injury, thanks to its ability to block glutamate release; ii) it is able to reduce the reactive astrocytes in order to balance the astroglial scarring, given its ability to reduce inflammation and act directly on the astrocytes; iii) it is able to stimulate OD proliferation in order to replace the apoptotic ODs.

Effects of BoNT/A on Spinal Cord Regeneration and Locomotor Recovery (Experiments)

The experimental procedure considers the behavioural observation and evaluation of motor recovery with the BMS scale (Basso D M, Fisher L C, Anderson A J, Jakeman L B, McTigue D M, Popovich P G (2006) Basso Mouse Scale for locomotion detects differences in recovery after spinal cord injury in five common mouse strains. J Neurotrauma 23, 635-659) and the sensitivity restoration (tail-flick test) in the murine model of SCI in mice that were injected intrathecally with BoNT/A or saline solution (i.th.-spinal) within 1 hour of the lesion. An immunohistochemical analysis was performed 7, 30 and 60 days after SCI to evaluate:
  long-term effect of BoNT/A;
  reduction of the astroglial scar by BoNT/A;
  reduction of apoptosis by BoNT/A;
  reduction of inflammatory events by BoNT/A;
  promotion of remyelination and regeneration by BoNT/A.

The experiments performed are described in detail below with reference to the accompanying drawings, wherein:

FIG. 1 shows the locomotor recovery after intrathecal injection of BoNT/A (A). BoNT/A (15 pg/5 microL) was administered within 1 hour after surgery and the first behavioural observation was made 24 hours after (D1). While mice injected with saline solution never recovered, animals treated with BoNT/A showed a significant improvement in the paraplegia ($p<0.0001$) just two days (D2) after SCI and reached a total motor recovery (BMS score 9) 30 days after spinal injury. Sensitivity recovery after intrathecal injection of BoNT/A (B). The administration of BoNT/A resulted in a gradual and significant (D2-D3 $p<0.05$; D4-D7-$p<0.001$; mice treated with BoNT/A vs saline and vs baseline—BL) restoration of the thermal threshold up to full recovery (D10 $p<0.0001$) that persists until the final behavioural observation (D30). In contrast, mice treated with saline solution after surgery reached the latency threshold limit (10 sec) and never showed an improvement in thermal sensitivity.

Figure 2:
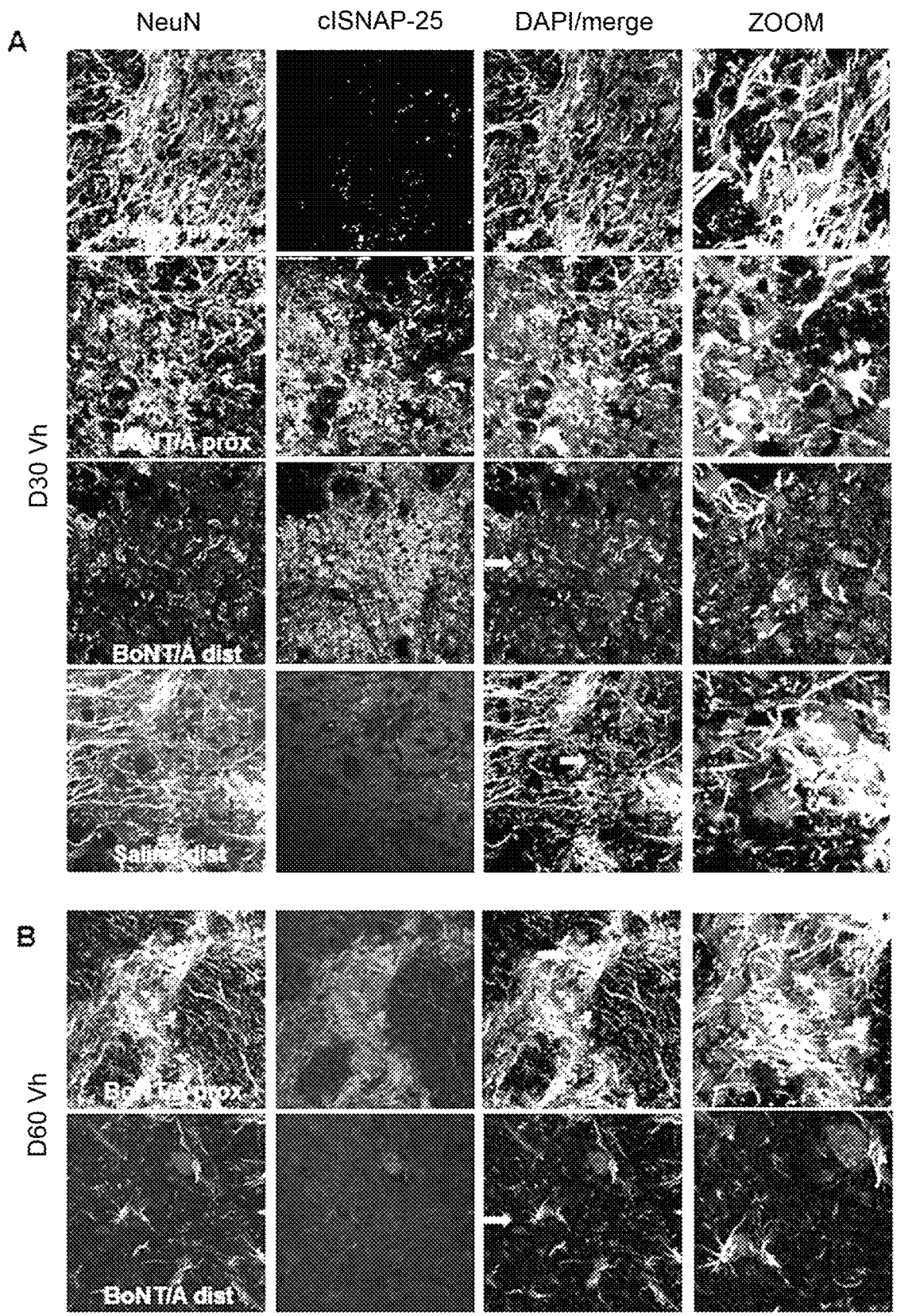

FIG. 2 shows confocal images of tissue samples proximal (prox) and distal (dist) with respect to the lesion, collected 30 (D30—panel (A) and 60 (D60—panel B) days after injury. Expression of GFAP revealed a large astrogliosis both proximal and distal to the lesion in mice treated with saline solution, while in mice treated with BoNT/A it was only detectable in the proximal area. Expression of cl-SNAP25 highlighted the long-term action of BoNT/A at D30 and D60 both in the proximal and the distal site and co-localization with GFAP confirmed that astrocytes are a target of BoNT/A.

Figure 3:
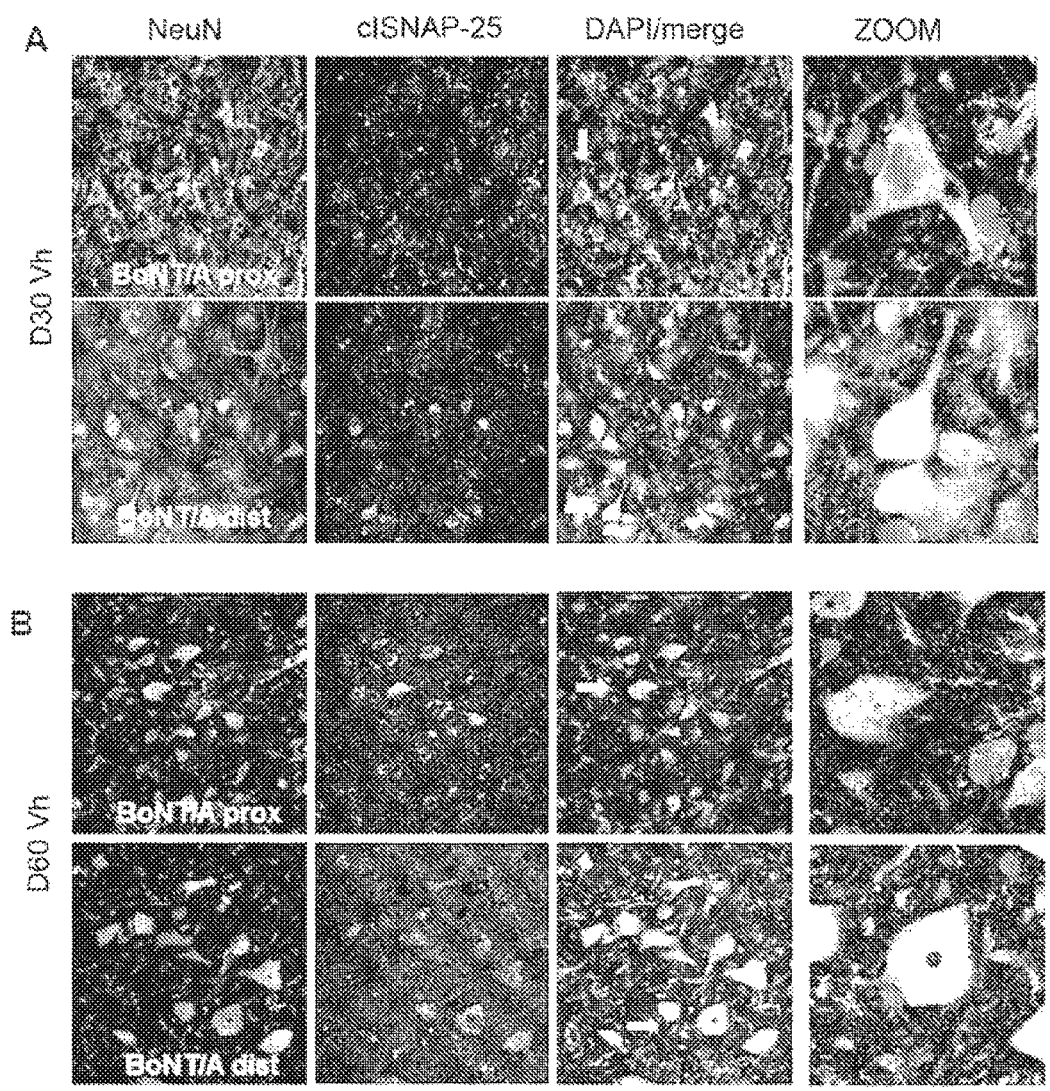

FIG. 3 shows confocal images of tissue samples proximal (prox) and distal (dist) with respect to the lesion, collected 30 (D30—panel (A) and 60 (D60—panel B) days after injury. Expression of NeuN showed intact neurons in the area proximal to the lesion in mice treated with BoNT/A, while in mice treated with saline solution the intact cell bodies were not visible (data not shown). Expression of cl-SNAP25 highlighted the long-term action of BoNT/A at D30 and D60 both in the proximal and the distal site and co-localization with NeuN confirmed that neurons are a target of BoNT/A.

Figure 4:
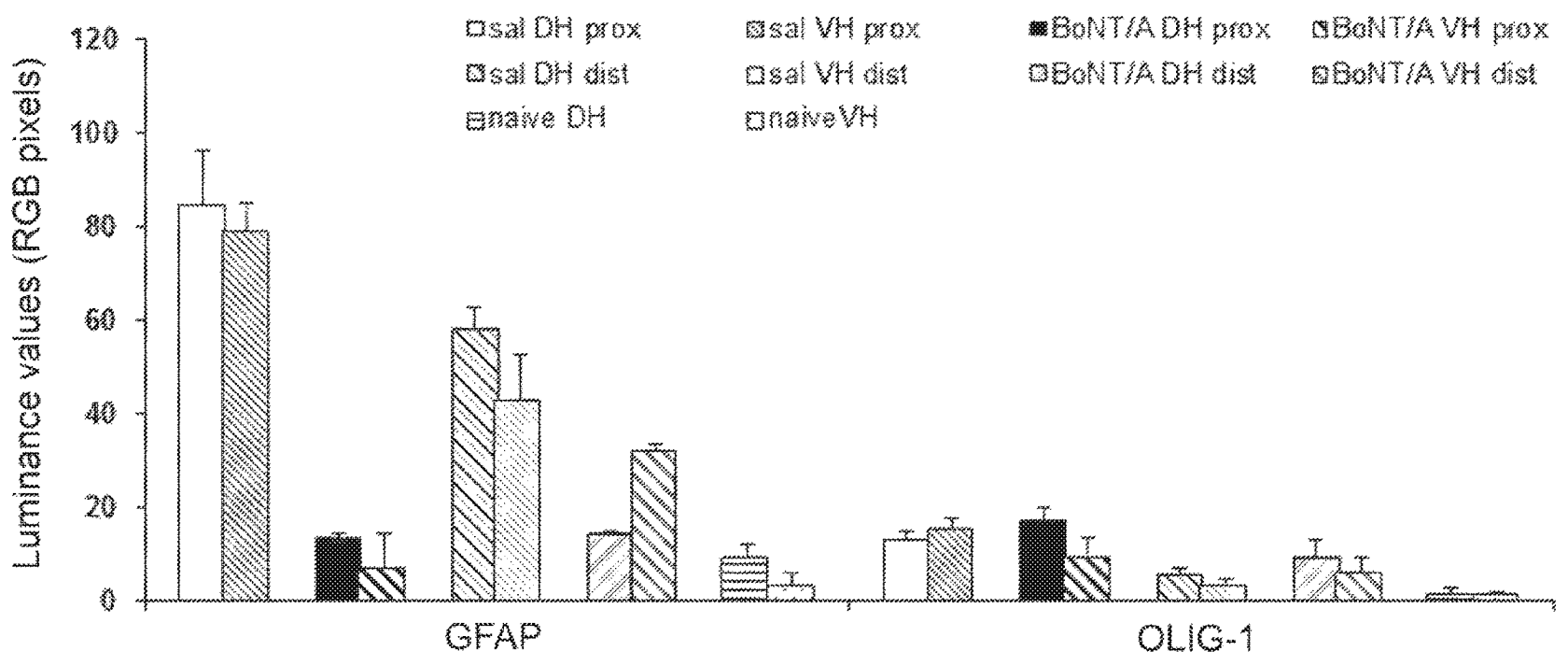

FIG. 4 shows the fluorescence analysis of GFAP and OLIG-1 expression 30 days after spinal injury. The graph shows a significant reduction ($p<0.0001$) of GFAP expression both in the dorsal horn (DH) and the ventral horn (VH) proximal and distal to the site of the lesion in comparison with mice treated with saline solution. The evaluation of the fluorescence of OLIG-1 shows a significant increase ($p<0.05$) of OLIG-1 expression in the distal part of the marrow both in the DH and the VH in animals treated with BoNT/A.

Figure 5:
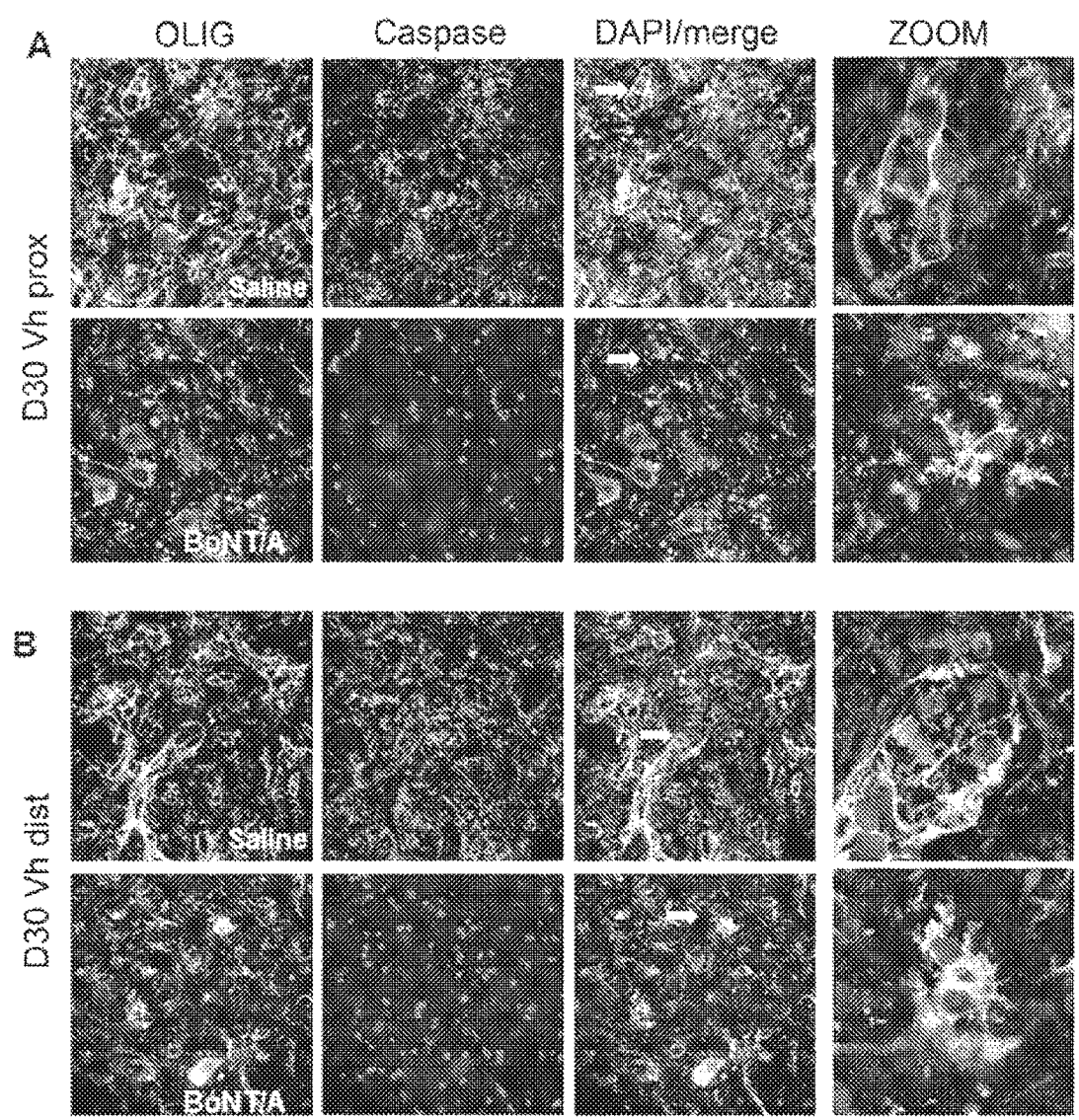

FIG. 5 shows OLIG-1 and cl-caspase expression in mice treated with saline solution and with BoNT/A 30 days after SCI proximal (A) and distal (B) to the site of the lesion. cl-caspase is an apoptosis marker that is particularly expressed in mice treated with saline solution and strongly reduced by administration of BoNT/A both at the distal and proximal level in SCI mice. cl-caspase staining in oligodendrocytes is particularly evident in mice treated with saline solution, while SCI mice treated with BoNT/A showed intact oligodendrocytes with little cl-caspase.

Figure 6:
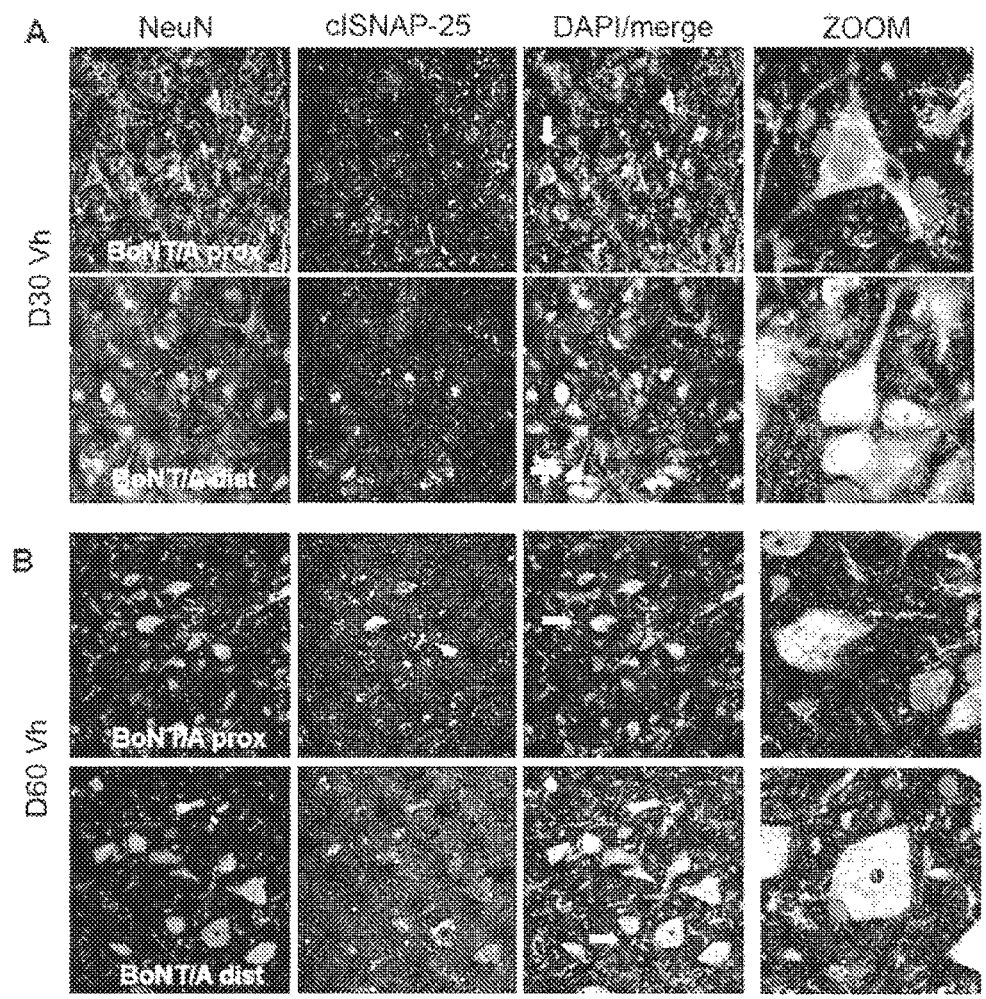
Figure 6:
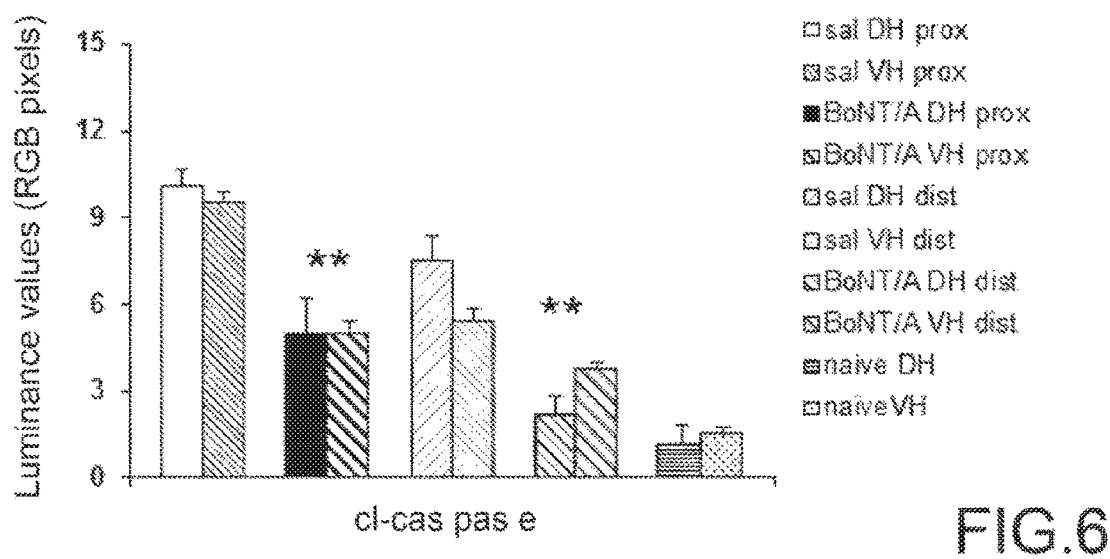

FIG. 6 shows NeuN and cl-caspase expression in mice treated with saline solution and with BoNT/A 30 days after SCI proximal (A) and distal (B) to the site of the lesion. NeuN is a neuron marker that allows us to observe the presence of intact neurons both in the proximal (FIG. 6a), and the distal (FIG. 6b) area in mice treated with BoNT/A, while in mice treated with saline solution the intact cell bodies are not detectable in either of the areas (FIGS. 6a and 6b).

The graph in FIG. 6c shows a significant reduction ($p<0.0001$) of cl-caspase expression both in the dorsal horn (DH) and the ventral horn (VH) proximal and distal to the site of the lesion in comparison with mice treated with saline solution.

Example 1

ANIMALS: CD1 female mice (Charles River Labs, Como, Italy) with an initial weight of approximately 30-35 g were used. Upon their arrival at the laboratory (at least 2 weeks before the experiments), the mice were housed in standard transparent plastic cages, in groups of 4 per cage, under standard conditions for animals (free access to food and water, 12:12 light/dark cycle, at a room temperature of 23° C.). The experiments were carried out between 11:00 am and 1:00 pm. The animals were treated and handled according to the guidelines of the Committee for Research and Ethical Issues of the IASP (PAIN® 1983, 16, 109-110) and the Italian and European laws (DLGs n.26 of Apr. 3, 2014, European Directive 2010/63/EU) on the protection of animals used for scientific research.

SURGERY: in order to cause the spinal cord injury, the animals were profoundly anaesthetized with a 1:1 mixture of Rompun (Bayer 20 mg/ml; 0.5 ml/kg) and Zoletil (100 mg/ml; 0.5 ml/kg), the hair of the back was shaved, the back disinfected with betadine and an incision was made to expose the backbone. The animals were mounted on a stereotactic apparatus with spinal adapters connected to an electronic cortical impactor designated as "PinPoint" (Stoelting), which allows with pinpoint accuracy for the application of a point force in the area to be injured, and maintained at 37° C. throughout the surgery.

In order to obtain a severe spinal trauma, the following parameters were set: —medium, rounded and flat tip (#4);—speed 3 m/sec;—depth 5 mm;—residence time 800 ms. The spinal cord was injured at the thoracic level 10 (T10) and no laminectomy was performed.

To identify potential anomalous cases, the analysis of graphic impact parameters was used, performed with the PinPoint software. Behavioural analyses were also carried out to corroborate the differences in the severity of the lesions within the groups. The mild lesions were excluded from the study on the basis of these criteria.

As post-operative treatment, the bladder was emptied by manual abdominal pressure twice a day until restoration of bladder function, and the prophylactic antibiotic treatment (Baytril 2.5 mg/kg) was maintained for 1 week. In the first 24 hours the animals were maintained at 37° with a heated plate, rehydrated with 1 ml of Ringer's lactate. To ensure feeding, wet food was placed in the cage.

TREATMENTS: for the intrathecal injection, a volume of 5 µl of saline (0.9% NaCl) or of BoNT/A solution (0.937-15 pgtox/mouse) was injected in the mice at the spinal level L1/L2 using a microsyringe within 1 hour of the SCI.

Behavioural Texts

The Basso Mouse Scale (BMS). The locomotor function of the hind legs was evaluated in the open field for all treatment groups. Mice were evaluated by two blinded evaluators. The BMS score (Basso D M, Fisher L C, Anderson A J, Jakeman L B, McTigue D M, Popovich P G (2006) Basso Mouse Scale for locomotion detects differences in recovery after spinal cord injury in five common mouse strains. J Neurotrauma 23, 635-659) goes from 0-9, where 0 indicates complete paralysis and 9 indicates normal movement of the hind legs. The performance of the right paw and that of the left one were averaged to obtain the BMS score. The mice were tested for functional deficiencies of the hind legs at 1, 2, 3, 4, 7, 10, 14, 17, 20, 30 (n=8/11 per group) after SCI. Only mice with BMS scores between 0-3, after surgery, were assigned to the experimental group classified as "severe" and used for the analyses that follow.

Tail Flick Test. The mice were tested under the same conditions, i.e. at 7:00 a.m.-9:00 a.m. after 15 minutes of acclimatization. The environment in which the test was carried out was thoroughly washed between one animal and the other to eliminate any smell related to stress signals. A radiant heat source with a locator light (Ugo Basile) was placed on the tail and the latency to withdrawal was determined. A cutoff time of 10 seconds was used to prevent tissue damage. The latency to withdrawal or to a flick of the tail away from the heat source was recorded with a built-in timer, which showed the reaction time in 0.01 second increments. The tests were carried out three times with a 5 minute rest between sequences, and the average latency was recorded. All tests were carried out by researchers blinded to the treatment.

Effects of BoNT/A on Paraplegia

The first day after surgery, the animals which had been administered BoNT/A and those which had been administered saline solution didn't have significantly different BMS scores (FIG. 1A). All animals in both groups showed no movement of the hind legs. After 4 days from surgery, only animals treated with BoNT/A showed an improvement in the locomotor function of the hind legs, with significantly higher open field scores (>3 points on the BMS scale) compared to those treated with saline ($p<0.0001$). After 4 weeks from surgery, the mice treated with BoNT/A had fully recovered the normal motor function, while the animals treated with saline were still totally paralysed ($p<0.0001$).

The animals treated with saline showed a total absence of thermal sensitivity after SCI. They always reached the latency threshold limit (10 sec) and they never recovered during the test period TF (FIG. 1B). On the other hand, the mice treated with BoNT/A began to restore the thermal threshold already two days after the injury and restored it completely at day 20 ($p<0.0001$).

Example 2

Immunohistochemistry

Seven or 30 days after SCI, three mice for each experimental group were sacrificed for immunohistochemical analysis and perfused with saline followed by 4% paraformaldehyde in phosphate buffered saline (PBS, pH 7.4). The thoracic spinal cord (T1-T13) of the mice was collected and kept in immersion for 48 hours in 4% paraformaldehyde in phosphate buffered saline (PBS, pH 7.4) after cryoprotection with 30% (w/v) sucrose solution in PBS and maintained at −80° C. Cryostat sections of 40 µm were obtained. For the double IF staining, different sections were incubated for 48 hours at room temperature with primary antibodies (see Table 2) in 0.3% Triton. The sections were then washed in PBS and incubated for 2 hours at room temperature with the secondary antibodies (see table). The sections were washed again in PBS and incubated for 10 minutes with Bisbenzimide (Hoechst 33258, 1:1000, Jackson ImmunoResearch) to stain the nuclei. After washing in PBS, the sections were mounted on slides.

TABLE 2

| | ANTIBODIES | | |
|---|---|---|---|
| | SPECIES | PRODUCT | MARKER |
| PRIMARY | | | |
| NeuN | Mouse monoclonal | 1:100 Millipore | Neurons |
| Cd11b | Rat monoclonal | 1:100 AbDSerotec | Microglia/Macrophages |
| GFAP | Mouse monoclonal | 1:100 Sigma-Aldrich | Astrocytes |

TABLE 2-continued

| | | ANTIBODIES | |
|---|---|---|---|
| | SPECIES | PRODUCT | MARKER |
| OLIG-1 | Mouse monoclonal | 1:100 Santa-Cruz | Oligodendrocytes |
| clSNAP-25 | Rabbit polyclonal | 1:100 Gift of Prof. C. Montecucco and Dr. O. Rossetto | Cut from SNAP-25 |
| Casp-cl | Rabbit polyclonal | 1:100 Cell signaling | Apoptosis |
| MBP | Rabbit polyclonal | 1:100 Sigma-Aldrich | SNC myelin |
| SECONDARY | | | |
| Alexa Fluor 488 | Donkey anti-mouse | 1:100 Jackson ImmunoResearch | Green |
| Cy2 | Donkey anti-rat | 1:100 Jackson ImmunoResearch | Green |
| Rhodamine | Goat anti-rabbit | 1:100 Jackson ImmunoResearch | Red |

Confocal Microscopy and Quantification of Immunoresponsive Cells

IF images at low magnification (10× objective) and high magnification (63× objective) from immunostained spinal cord sections were captured by confocal laser scanning microscopy using a TCS SP5 microscope (Leica Microsystems, Milan, Italy) connected to diagnostic instruments with a digital camera controlled by the LAS AF lite software from Leica Microsystems (free download available at www.leicamycrosystems.com).

All analyses were performed in the sequential scan mode to exclude overlap between channels. Quantifications were performed using the ImageJ software (version 1.41; National Institutes of Health, Bethesda, Md., United States of America). The number of IF-positive cells (nuclei) was counted automatically with the label counting machine, and then the average was calculated for each group of mice (n=3/group). The fluorescence was calculated with the RGB (red, green, blue) method, which converts RGB pixels into luminance values. 3 animals per group were considered and for each animal three sections were randomly selected and analysed by researchers blinded to the treatment.

For all groups, the distal (2-3 mm rostro-caudal with respect to the epicentre of the lesion) and proximal (impact area T9-T11) sections with respect to the site of the lesion and the dorsal (DH) and ventral (VH) horns were analysed separately.

Example 2 A

Long-Term Effects of BoNT/A

After being transported into the cytosol of neuronal cells, the light chain (LC) of BoNT/A cuts Receptor SNAP (Soluble NSF Attachment Protein) (SNARE) proteins in the cytosol leading to inhibition of exocytosis of neurotransmitter-carrying vesicles. LC/BoNTA was shown to be located on the neuronal cell membranes. Further studies showed that the localization of LC/BoNTA on the membranes was due to the high affinity binding with its substrate SNAP25 that is localized on the membranes. The heavy chain is essential for entering the axon endings, by binding the SV2 receptor, and for allowing entry of BoNT/A in neurons through the endocytosis process. The light chain, inside the cell, has protease activity and degrades SNAP-25, which is required for the formation of the SNARE complex and the subsequent vesicular release of neurotransmitters at the synaptic level.

One of the features of the BoNTs, particularly of serotype A, is the duration of action, 2-6 months, in patients, at concentrations in the fM or pM range. The mechanisms of this persistence of the effects are not yet clear. Anyway, the duration of the intracellular enzymatic activity of BoNT/A in rat spinal cord neurons was shown to be at least 10 months (Whitemarsh R C, Tepp W H, Johnson E A, Pellett S. (2014) Persistence of botulinum neurotoxin a subtypes 1-5 in primary rat spinal cord cells. PLoS One. 9(2):e90252). This feature gives BoNT/A an advantage compared to common drugs, which need to be administered continuously so that their therapeutic effects are maintained.

Thanks to this mechanism of action, BoNT/A, which cuts SNAP-25, is extremely promising as a therapeutic treatment for lesions caused by SCI.

Evaluation of the Presence of Cut SNAP25 in the Marrow 30 and 60 Days After SCI The inventors labelled cl-SNAP25 in the spinal cord of injured mice treated with BoNT/A or saline solution, to check if BoNT/A was still active 30 and 60 days after the i.th administration, which cells were suffering from poisoning by BoNT/A, and if BoNT/A reached sites distal to the injection spot. cl-SNAP25 was detected only in the tissue of mice treated with BoNT/A and was totally absent from the spinal cord of mice treated with saline solution (FIG. 2A, B); activated astrocytes and neurons (FIG. 3A, B) were rich in cl-SNAP25 and BoNT/A decreased astrogliosis in the area distal to the lesion.

Example II B

BoNT/A Decreases Astrogliosis

The thirtieth day after SCI, in mice, can be considered as the end of the subacute/intermediate phase and the beginning of the chronic phase. As evident in mice treated with saline solution (FIG. 2 and FIG. 4), this transition period features maturation/stabilization of the lesion, including continuous formation of a scar and development of cysts and/or syringomyelia (pathological tubular cavities in the organism), and is accompanied by alterations in neuronal circuits. A somewhat delayed astrocytic response starts in the subacute phase (within the first 7 days), during which the astrocytes at the lesion periphery become hypertrophic and proliferative, which correlates with a dramatic increase in the expression of the astrocyte intermediate filament, GFAP. These reactive astrocytes cause the growth of multiple large cytoplasmic processes that interconnect forming the astrocytic (gliotic) scar, particularly evident in mice treated with saline solution (FIG. 2A), but strongly reduced by treatment with BoNT/A (FIG. 2B). Also the expression of GFAP revealed this significant difference both in the proximal and the distal part of the lesion site (p<0.001; FIG. 3), demonstrating the powerful anti-astrogliosis action of BoNT/A both proximal and distal to the lesion.

Example II C

BoNT/A Protects Oligodendrocytes and Promotes Remyelination (OLIG-MBP)

Co-staining with OLIG-1 (30 days after SCI) showed a dramatic increase of dystrophic oligodendrocytes, along the epicentre of the lesion, in particular the oligodendrocyte marker was highly co-localized with cl-caspase 3 which is a cell death indicator (FIG. 5). In SCI mice treated with BoNT/A a few important morphological changes were evident. In particular, OLIG-1 staining revealed intact cell bodies in the epicentre area, differently from the devastated area observed in mice treated with saline solution. In addition, a high expression of OLIG-1, in comparison to naive animals (graph shown in FIG. 4, presumably oligodendrocyte precursor cells—OPCs, and NG2 glia) was evident on the cavity perimeter, which contains cl-caspase 3-positive debris and necrotic tissue forming a dense network around it.

Thirty days after SCI, the expression of cl-caspase 3 was dramatically high in mice treated with saline (FIG. 6C) both in the distal and the proximal zone, while treatment with BoNT/A counteracted apoptosis that, in the distal part, was close to the level found in naive mice (p<0.01).

In this stage, severe and irreversible damage occurs in mice treated with saline solution: neurons proximal to the lesion epicentre collapse (FIG. 6a) and neuronal bodies are practically absent from, or barely detectable in, the distal areas (FIG. 6b). Instead, treatment with BoNT/A allowed for the sparing of a few neurons from death (FIG. 6a) in the vicinity of the impact area and the sparing of a large number thereof in the distal areas (FIG. 6b).

What is claimed is:

1. A method of treating paralysis caused by spinal cord traumatic injury in a patient resulting from direct mechanical trauma, and spinal cord traumatic injury resulting in tissue damage characterized by (i) astroglial scarring, (ii) destruction of neurons caused by excitotoxicity, and (iii) apoptosis of oligodendrocytes and chronic demyelination, wherein paralysis includes total absence of motor recovery in the patient, the method comprising:
administering to the patient a therapeutically effective amount of botulinum neurotoxin serotype A, wherein the therapeutic treatment comprises intrathecal administration of botulinum neurotoxin serotype A; and,
treating the paralysis by: (i) protecting neuronal cells from excitotoxicity after injury by blocking glutamate release, (ii) reducing reactive astrocytes in order to balance the astroglial scarring by reducing inflammation and acting directly on the astrocytes, and (iii) stimulating oligodendrocytes proliferation in order to replace apoptotic oligodendrocytes.

2. The method according to claim 1, wherein botulinum neurotoxin serotype A is selected from the group consisting of botulinum neurotoxin serotype A1 and botulinum neurotoxin serotype A2.

3. The method according to claim 1, wherein the paralysis is paraplegia or tetraplegia.

4. The method according to claim 1, wherein the intrathecal administration is carried out by injection in the vertebral area immediately caudal to the area affected by said spinal cord injury.

5. The method according to claim 1, wherein the patient is a human being.

6. The method according to claim 1, wherein the pharmaceutically effective amount of botulinum neurotoxin serotype A is in the range of from 75 units to 360 units.

* * * * *